United States Patent [19]

Nickell

[11] 3,992,186

[45] Nov. 16, 1976

[54] TETRAHYDROFUROIC HYDRAZIDE FOR RIPENING SUGARCANE

[75] Inventor: Louis G. Nickell, Honolulu, Hawaii

[73] Assignee: Hawaiian Sugar Planters Association, Honolulu, Hawaii

[22] Filed: Apr. 5, 1974

[21] Appl. No.: 458,430

[52] U.S. Cl. .................................. 71/88; 260/347.3; 260/347.4
[51] Int. Cl.$^2$ .......................................... A01N 9/00
[58] Field of Search ...................... 71/88; 260/347.3

[56] References Cited

UNITED STATES PATENTS

| | | | |
|---|---|---|---|
| 3,352,663 | 11/1967 | Freund et al. | 71/88 |
| 3,393,209 | 7/1968 | Majewski | 71/88 |
| 3,821,261 | 6/1974 | Kaugars | 71/88 |

OTHER PUBLICATIONS

Nickell et al., "Effects of Chemicals on Ripening, etc.;" (1965), Hawaiian Sugar Tech. 24th Ann. Conf., pp. 152–163 (1965).
Cook et al., "[4,5-c] Furothropone" (1968); Tetrahedron 24, pp. 4501–4508 (1968).

*Primary Examiner*—Glennon H. Hollrah
*Attorney, Agent, or Firm*—Burns, Doane, Swecker & Mathis

[57] ABSTRACT

Sucrose yield of sugarcane is increased by treating the cane crop a few weeks prior to harvest with a novel ripening agent, namely, with tetrahydrofuroic hydrazide or with certain of its novel derivatives.

5 Claims, No Drawings

TETRAHYDROFUROIC HYDRAZIDE FOR RIPENING SUGARCANE

BACKGROUND OF INVENTION

Because of the world's limited land and food resources, there has been an ever growing interest in increasing the yield of food-bearing plants. As sugar is among the principal foods for man and animals, as well as a commercially important food for fermentation organisms, it is only natural that much effort continues to be devoted to increasing the sucrose yield of sugarcane in a variety of ways, such as by improvement of the varieties of cane being planted, by enrichment of the soil with fertilizers and by irrigation where natural moisture was insufficient for optimum plant growth. In the past decade or two scientists seeking to increase sugar production have increasingly investigated the use of a variety of chemicals in efforts to modify and control the physiological processes of sugarcane, particularly its ripening prior to harvest.

Some of the more successful prior efforts are disclosed in U.S. Pat. Nos. 3,224,865; 3,245,775; 3,291,592; 3,482,959; 3,482,961; 3,493,361; 3,505,056; 3,660,072 and 3,671,219. However, failures continue to outnumber successes by a wide margin and a dependable rule for predicting utility of a given compound or chemical structure continues to elude those working in this art. Because of concern about the resistance of some compounds to breakdown in the plant and their persistence in the soil, their deliberate application to sugarcane has generally been viewed with misgivings pending proof of their non-toxicity, unless the intended use of the sugar product is industrial, e.g., in a fermentation process, rather than nutritive. Accordingly, the search for new sugarcane ripeners continues unabated.

Generally speaking, chemicals selected for evaluation have been of a type which has been previously found active in work with other plants as a plant hormone, herbicide or inhibitor of growth of terminal buds, or active in killing the spindle of cane upon topical microapplication, etc. However, among the compounds heretofore known to be useful for such other special purposes only a few are found to be effective in controlling the ripening of sugarcane in the desirable manner. No predictable relationship has yet been recognized between (a) the chemical structure of such compounds, (b) their phytotoxic effects, or (c) their physiological effects on the morphogenetic development of the plant, on the one hand, and their activity in having positive effects on ripening, on the other hand. In other words, the effectiveness of a compound in controlling the ripening of sugarcane and thereby increasing sugar yield remains essentially unpredictable, and the search for suitable chemical ripeners continues to be fundamentally empirical.

OBJECTS OF THE INVENTION

It is an object of this invention to provide a new type of agent for modifying the physiological growth of plants, and more particularly for controlling the ripening of sugarcane. A more specific object is to increase the sucrose yield of sugarcane by chemically treating it during its final ripening stages prior to harvest without introducing substantial toxicological hazards, and preferably without causing any visible damage to the cane plant such as drying of its spindle or of the leaf. Still more specifically it is an object of this invention to increase the sucrose yield of sugarcane by treating it a few weeks prior to harvest with a chemical agent which is sufficiently stable to provide the desired effect over a period of many weeks and thereby give adequate operationsl flexibility, but yet has a relatively low degree of persistence and is susceptible to autodecomposition or to decomposition by soil bacteria. A compound which increases the sucrose content only temporarily over a period of three weeks or less after application and then results in a substantial decrease is usually not a desirable chemical ripener except in situations where harvesting time can be rigidly programmed in advance in relation to the time of application of the chemical ripener.

SUMMARY OF INVENTION

According to the present invention a novel type of chemical ripening agent has been obtained. More specifically, excellent results in increasing the sucrose yield of sugarcane are obtained by applying tetrahydrofuroic hydrazide (THFH) to sugarcane, i.e., to the younger, growing parts of the cane stalk. Good results are also obtained by similarly applying certain of its derivatives, e.g., 2,6-dichlorobenzaldehyde tetrahydro-2-furoyl hydrazone (DBTH).

The preferred usage form is a mixture containing the selected tetrahydrofuran derivative, e.g., THFH or DBTH in an aqueous solution or suspension utilizing one or a combination of known surface active agents commonly and variously used in the prior art as wetting agents, detergents or emulsifying agents. However, dry dusting compositions containing THFH or DBTH and a solid diluent such as clay are also useful.

THFH, $C_5H_{10}O_2N_2$, (molecular weight 130.15, boiling point 131° C./1.4 mm Hg), which is the most active material of the present invention, has a structure corresponding to the following formula

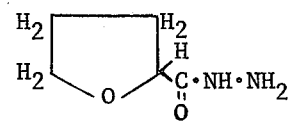

Among its derivatives tested to date, only 2,6-dichlorobenzaldehyde tetrahydro-2-furoyl hydrazone (DBTH) has also shown good activity, DBTH, $C_{12}H_{12}O_2N_2Cl_2$, (molecular weight 286.9, melting point 154°–156° C.) has a structure corresponding to the following formula

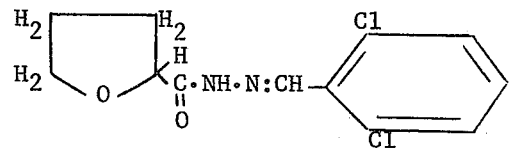

The present discovery of the effective ripening activity of these compounds is astonishing, as of the other twenty-three related furan and tetrahydrofuran derivatives heretofore tested twenty-one have been found to be inactive and only two, 5-nitro-2-acetylfuran and 5-nitro-furfurylidene diacetate, only slightly active in ripening sugarcane and not of practical value for this purpose. The latter two compounds are shown among the list of compounds which were tested in Hawaii as potential sugar ripeners some ten years ago, as reported by L. G. Nickell and T. T. Tanimoto in the 1965 Reports, Hawaiian Sugar Technologists, pp. 152–166.

THFH can be made from tetrahydrofurfuryl alcohol by classical procedures of organic synthesis. According to one such procedure, for instance, the alcohol is first oxidized to form the corresponding monocarboxylic acid, the resulting tetrahydrofuroic acid is esterified with methanol to produce tetrahydrofuroate, the latter is dissolved in methanol, the solution is mixed and refluxed with one mole equivalent of hydrazine hydrate, excess methanol is removed by distillation and finally the residue is distilled under reduced pressure to yield tetrahydrofuroic hydrazide, THFH. This preparation of THFH proceeds according to the following equation:

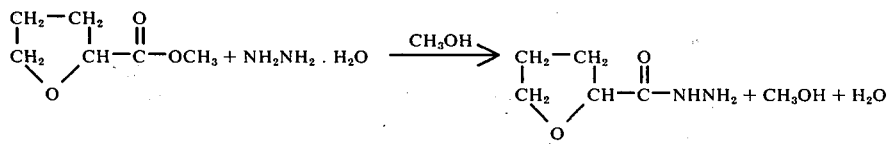

DBTH can be made from THFH by reacting the latter with 2,6-dichlorobenzaldehyde according to otherwise well-known procedures. See, for instance, F. C. Whitmore, Organic Chemistry, Vol. Two, Second Edition, Dover Publications, New York (1951), p. 678.

In accordance with this invention, the sugarcane crop is treated with THFH or DBTH or with a composition containing same at any time some two to ten weeks before harvest, the preferred time for treatment being between about 3 and 8 weeks prior to harvest.

Good results are obtained when the sugarcane crop is treated at a rate in the range of from 1 to 4 pounds of THFH or DBTH per acre of sugarcane. However, higher rates (e.g., up to about 80 pounds THFH or DBTH, or more, per acre) or rates lower than 1 pound per acre can also be used. The optimum amount will vary somewhat depending on the particular mode of application, environmental conditions, time of year, and age and variety of cane being treated, but can be readily determined for each particular case by preliminary testing.

The active agent is conveniently applied in the field in the form of an aqueous solution, emulsion or suspension, i.e., a liquid composition which may be sprayed from a boomspray, or it can be dusted on from an airplane or the like as a dust composition which contains the active compound diluted with an inert solid such as clay. In preparing suitable liquid compositions, surface active agents of the type described, for instance, in U.S. Pat. No. 3,224,865, column 2, lines 61–66 or in U.S. Pat. No. 3,245,775, column 2, lines 57–64 are convenient to use. The preferred surfactants for use in liquid compositions of the present invention are those of the non-ionic type, e.g., alkyl phenoxy poly(ethylene-oxy)ethanols such as adducts of nonylphenol and ethylene oxide; trimethyl nonyl polyethylene glycol ethers; polyethylene oxide adducts of fatty and resin acids, and long chain alkyl mercaptan adducts with ethylene oxide.

With the type of boom-spray apparatus used in this work, it has been found convenient to apply the THFH or its derivative to the sugarcane field in the form of an aqueous solution, suspension or emulsion having a concentration of active agent such that the application at the rate of from 5 to 20 gallons of liquid composition per acre will provide the required dosage of active chemical. Thus, for instance, the treating mixture may contain from about 3 to 25% by weight THFH dissolved or dispersed in water. However, application rates of less than 5 or more than 20 gallons per acre may be preferred when a different dispensing mechanism is used.

The preferred carrier for the active ripening agent is water to which about 0.1 to 2% by weight of surface active agent has been added. However, instead of using water as the carrier, non-phytotoxic mineral oils either as such or in the form of water-in-oil or oil-in-water emulsions may be used similarly in accordance with practices which are otherwise well known in the art of treating vegetation in the field with beneficial growth control agents. Excellent results are obtained when the tetrahydrofuran derivative of this invention is present as essentially the sole active ingredient in the treating composition, but it may also be applied in combination with other ripeners.

DESCRIPTION OF SPECIFIC EMBODIMENTS

EXAMPLE 1

Part A — Preparation of THFH 130 gm (1 mole) methyl tetrahydrofuroate was dissolved in 200 ml methanol and 50 gm (1 mole) hydrazine hydrate was added thereto. The solution was refluxed for 2 hours. At the end of this period the excess methanol was removed by distillation and the residue was distilled in vacuo to yield 135 gm (92.5%) THFH, b.p. 131° C./1.4 mm Hg.

Analysis for $C_5H_{10}O_2N_2$: Calculated N, 21.53%. Found N, 21.40%.

Part B — Preparation of THFH Treating Solution

Weigh out 1 gram of THFH and dissolve weighed material in approximately 6 ml of water. Dilute this solution with water to exactly 8 ml. Add 1 drop of Tergitol NPX surfactant with medicine dropper to diluted solution. Agitate by shaking. Solution is now ready for application.

Part C — Application of THFH Composition to Cane 0.3 ml of the aqueous THFH solution prepared as described in Part B above was applied in a test plot in a commercial cane field in Hawaii by means of a syringe with a fine needle on the spindle area at the top of the last visible dewlap of each of 20 stalks of sugarcane.

Another group of 20 stalks in the same test plot were treated in an identical manner with "Trysben" (dimethylamine salt of trichlorobenzoic acid), used as a standard because of its known and consistent good activity.

The date of application of the ripener solutions was Jan. 18, and the age of the cane at the time of application was 20.25 months.

A set of 10 of these treated stalks from each group were harvested 4 weeks after such treatment and another set of 10 were harvested 5 weeks after such treatment. At each harvest a set of 10 untreated stalks from the same plot were also harvested as a control.

The top 15 joints of each 10-stalk set of the treated stalks, as well as those of untreated control stalks from the same test plot, were removed, and each set was combined and analyzed in terms of juice purity and pol percent cane, following the so-called "press method" developed by T. Tanimoto, Hawaiian Planters' Record, 57, 133 (1964). "Pol percent cane" is a polarimetric determination and equals the percentage of sucrose if sucrose is the only optically active substance in the solution. In any event, determination of the pol percent cane is a standard and effective method for determining the sucrose content of sugarcane. The results are given in Table I.

The data show a very significant increase in sucrose yield in the cane which was treated with the chemical ripeners. THFH produced a better sucrose yield than Trysben in the case of cane harvested 4 weeks after treatment although Trysben produced a greater increase in the cane which was harvested 5 weeks after treatment in this test series. In either case THFH increased the sucrose yield by more than 7% over the sucrose available from the untreated control.

TABLE I

Cane Variety: H50 - 7209  
Age at Treatment: 20.25 months  
Date of Treatment: January 18

| | Harvest Time | | | |
|---|---|---|---|---|
| | 4 Weeks After Treatment | | 5 Weeks After Treatment | |
| Ripening Agent | Juice Purity | Pol % Cane | Juice Purity | Pol % Cane |
| THFH 0.3 ml (= 38mg/stalk)* | 86.59 | 11.40 | 85.21 | 12.59 |
| Trysben (standard) | 83.07 | 11.30 | 86.95 | 13.55 |
| Control (untreated) | 80.88 | 10.64 | 82.88 | 11.17 |

*Equivalent to an application of 4 lbs THFH per acre.

Part D

The effect of the ripener is of course somewhat dependent on the variety and age of the cane being treated, the amount of ripener applied, the weather conditions between treatment and harvest time, and so on. This is illustrated by the data shown in Tables II - VI below. In obtaining the data reported in these tables the same procedure was followed as that described in Part C, except that the amount of THFH applied to each stalk in the various test series was varied as shown in each of these tables.

TABLE II

Cane Variety: H49 - 3533  
Age at Treatment: 24.0 months  
Date of Treatment: May 5

| | Harvest Time | | | |
|---|---|---|---|---|
| | 4 Weeks After Treatment | | 5 Weeks After Treatment | |
| Ripening Agent | Juice Purity | Pol % Cane | Juice Purity | Pol % Cane |
| THFH 38 mg/stalk (4 lbs/acre) | 80.57 | 10.89 | 85.75 | 13.31 |
| Trysben (standard) | 78.22 | 9.96 | 76.96 | 9.59 |
| Control (untreated | 71.27 | 8.16 | 80.33 | 10.44 |

TABLE III

Cane Variety: H50 - 7209  
Age at Treatment: 21.25 months  
Date of Treatment: August 14

| | Harvest Time | | | |
|---|---|---|---|---|
| | 4 Weeks After Treatment | | 5 Weeks After Treatment | |
| Ripening Agent | Juice Purity | Pol % Cane | Juice Purity | Pol % Cane |
| THFH 38 mg/stalk (4 lbs/acre) | 70.13 | 8.49 | 81.46 | 11.80 |
| Trysben (standard) | 83.50 | 11.66 | 84.64 | 12.44 |
| Control (untreated) | 61.15 | 5.64 | 64.10 | 6.87 |

TABLE IV

Cane Variety: H50 - 7209  
Age at Treatment: 23.75 months  
Date of Treatment: October 13

| | Harvest Time | | | |
|---|---|---|---|---|
| | 4 Weeks After Treatment | | 5 Weeks After Treatment | |
| Ripening Agent | Juice Purity | Pol % Cane | Juice Purity | Pol % Cane |
| THFH 38 mg/stalk | | | | |

TABLE IV-continued

Cane Variety: H50 - 7209
Age at Treatment: 23.75 months
Date of Treatment: October 13

| | Harvest Time | | | |
|---|---|---|---|---|
| | 4 Weeks After Treatment | | 5 Weeks After Treatment | |
| Ripening Agent | Juice Purity | Pol % Cane | Juice Purity | Pol % Cane |
| (4 lbs/acre) | 77.58 | 10.29 | 72.99 | 7.99 |
| THFH 19 mg/stalk | | | | |
| (2 lbs/acre) | 76.45 | 9.26 | 77.44 | 9.17 |
| Trysben (standard) | 67.84 | 7.65 | 76.21 | 8.72 |
| Control (untreated) | 67.97 | 7.72 | 70.46 | 7.70 |

TABLE V

Cane Variety: H59 - 3775
Age at Treatment: 20.5 months
Date of Treatment: January 23

| | Harvest Time | | | |
|---|---|---|---|---|
| | 4 Weeks After Treatment | | 5 Weeks After Treatment | |
| Ripening Agent | Juice Purity | Pol % Cane | Juice Purity | Pol % Cane |
| THFH 19 mg/stalk | | | | |
| (2 lbs/acre) | 82.86 | 11.14 | 82.80 | 11.38 |
| THFH 9.5 mg/stalk | | | | |
| (1 lb/acre) | 74.79 | 8.31 | 81.44 | 10.52 |
| Trysben (standard) | 73.40 | 8.45 | 80.62 | 10.78 |
| Control (untreated) | 76.25 | 9.31 | 78.40 | 9.53 |

TABLE VI

Cane Variety: H50 - 7209
Age at Treatment: 22.5 months
Date of Treatment: July 18

| | Harvest Time | | | |
|---|---|---|---|---|
| | 4 Weeks After Treatment | | 5 Weeks After Treatment | |
| Ripening Agent | Juice Purity | Pol % Cane | Juice Purity | Pol % Cane |
| THFH 38 mg/stalk | | | | |
| (4 lbs/acre) | 77.69 | 9.92 | 81.02 | 10.92 |
| THFH 76 mg/stalk | | | | |
| (8 lbs/acre) | 72.21 | 8.39 | 79.92 | 9.59 |
| Trysben (standard) | 74.71 | 8.96 | 78.31 | 10.30 |
| Control (untreated) | 64.24 | 6.57 | 67.32 | 7.19 |

The tabulated data show that in each test series the application of THFH produced a very important increase in sucrose yield over that obtained in the untreated control. In many cases THFH produced a very much larger increase in sucrose yield than that produced by Trysben.

The data also show that THFH is effective over a wide range of concentrations and maintains its activity fairly constant over many weeks and that the benefits of the present invention can be obtained with similar effect at various stages of natural maturity of the cane at the time of treatment or harvest.

EXAMPLE 2

Application of DBTH Composition To Cane 0.3 ml of an aqueous DBTH solution, prepared as described above in Example 1, Part B in connection with THFH, was applied in screening tests to a test plot of sugarcane in essentially the same manner as described above in Example 1, Part C. A significant increase in sugar yield was noted in the case of the cane stalks treated with DBTH as compared with the untreated control stalks.

The nature, scope, utility and effectiveness of the present invention have been described and exemplified in the foregoing specification. However, these examples are not intended to be limiting and the true scope of the invention which is entitled to patent protection is particularly pointed out in the appended claims.

What is claimed is:

1. A process for modifying the ripening of field grown sugarcane so as to increase its yield of sucrose which comprises applying tetrahydrofuroic hydrazide in a sucrose increasing amount to the cane at a time from 2 to 10 weeks prior to harvest.

2. A process according to claim 1 wherein tetrahydrofuroic hydrazide is applied to the cane in admixture with water as a carrier.

3. A process according to claim 1 wherein tetrahydrofuroic hydrazide is applied to the cane in the form of an aqueous solution or suspension at the rate of 5 to 20 gallons of aqueous composition per acre.

4. A process according to claim 3 wherein the aqueous composition contains between 0.1 and 2% by weight of a surface active agent.

5. A process according to claim 3 wherein the aqueous composition contains between 0.1 and 2% by weight of a non-ionic surface active agent.

* * * * *